United States Patent [19]

Nadler

[11] Patent Number: 5,354,908

[45] Date of Patent: Oct. 11, 1994

[54] METHOD AND SYSTEM FOR COBALT ABSORPTION IN A HYDROFORMYLATION PROCESS

[75] Inventor: Kirk C. Nadler, Somerville, N.J.

[73] Assignee: Exxon Chemical Patents Inc., Linden, N.J.

[21] Appl. No.: 93,421

[22] Filed: Jul. 16, 1993

[51] Int. Cl.$^5$ .............................................. C07C 45/50
[52] U.S. Cl. .................................. 568/451; 568/426; 568/449
[58] Field of Search ..................... 568/451, 452, 449

[56] References Cited

U.S. PATENT DOCUMENTS

| | | | |
|---|---|---|---|
| 2,744,921 | 5/1956 | Mertzweiler et al. | 260/414 |
| 2,816,933 | 12/1957 | Mertzweiler | 260/638 |
| 3,520,937 | 7/1970 | Moell et al. | 260/604 |
| 3,725,534 | 4/1973 | Reisch | 423/417 |
| 3,941,848 | 3/1976 | Kummer et al. | 260/604 HF |
| 4,390,473 | 6/1983 | Cooper | 260/429 R |
| 4,625,067 | 11/1986 | Hanin | 568/451 |
| 5,091,599 | 2/1992 | DeMunck et al. | 568/882 |

FOREIGN PATENT DOCUMENTS 0391650 10/1990 European Pat. Off. ...... C07C 29/16

OTHER PUBLICATIONS

Hans Lemke, "Select Best Oxo Catalyst Cycle", *Hydrocarbon Processing*, Feb., 1966, vol. 45, No. 2, pp. 148–152.

*Primary Examiner*—Werren B. Lone
*Attorney, Agent, or Firm*—J. J. Mahon

[57] ABSTRACT

A method for absorbing cobalt within an olefinic feedstock which comprises the steps of introducing a volatile cobalt compound and an olefinic feedstock into an absorber to form a cobalt-containing olefin mixture, withdrawing the cobalt-containing olefin mixture from the absorber, introducing at least a portion of the cobalt-containing olefin mixture into a reactor, wherein a substantial portion of the volatile cobalt compound entrained within the cobalt-containing olefin mixture decomposes to its non-volatile cobalt compound species, and recycling this mixture back to the absorber so that it can be used to further absorb volatile cobalt such that a more concentrated cobalt-containing olefin solution is formed.

15 Claims, 4 Drawing Sheets

METHOD AND SYSTEM FOR COBALT ABSORPTION IN A HYDROFORMYLATION PROCESS

The present invention generally relates to a method for producing concentrated solutions of cobalt in the feed olefins used in a hydroformylation reaction. In particular, the cobalt absorber has a recycle means comprising a liquid hold-up tank or reactor whose operating conditions can be adjusted such that volatile cobalt compound (e.g., $HCo(CO)_4$) decomposes to a non-volatile cobalt compound species (e.g., $Co_2(CO)_8$).

BACKGROUND OF THE INVENTION

Hydroformylation reactions involve the preparation of oxygenated organic compounds by the reaction of carbon monoxide and hydrogen (a.k.a., syn gas or synthesis gas) with carbon compounds containing olefinic unsaturation. The reaction is performed in the presence of a carbonylation catalyst and resulting in the formation of a compound, for example, an aldehyde, which has one more carbon atom in its molecular structure than the starting olefinic feedstock. By way of example, higher alcohols may be produced in the so-called "oxo" process by hydroformylation of commercial $C_6$–$C_{12}$ olefin fractions to an aldehyde-containing oxonation product, which on hydrogenation yields respective $C_7$–$C_{13}$ saturated alcohols. The crude product of the hydroformylation reaction will contain catalyst, aldehydes, alcohols, unreacted feed, syn gas and by-products.

Before further processing of the crude product is possible, it is necessary to remove the catalyst therefrom. One conventional method of removing cobalt values from such a crude product is to treat the product with an alkali or acid wash technique. See U.S. Pat. No. 3,725,534 (Reisch), which issued on Apr. 3, 1973. However, this approach uses expensive raw materials and incurs problems associated with finally removing essentially all traces of cobalt from the water wash streams before being discharged.

Another conventional method involves the oxidation of the cobalt catalytic species followed by extraction as a cobalt salt in aqueous solution. See U.S. Pat. No. 2,744,921 (Mertzweiller et al.), which issued on May 8, 1956.

U.S. Pat. No. 4,625,067 (Hanin), which issued on Nov. 25, 1986, discloses still another method which involves the contacting of the crude product with a stream of stripping gas to entrain volatile cobalt, characterized in that the contacting is performed in the presence of water and aqueous acid to dissolve those cobalt values not entrained in the gas under the conditions of temperature and pressure employed for the contacting, and the aqueous phase is subsequently separated from the organic hydroformylation reaction product.

Although the stripping method disclosed in the Hanin patent overcomes the disposal and chemical additive costs of the caustic/acidification method of Reisch, it has the disadvantage that low concentrations of cobalt are absorbed into the olefinic feedstock per unit volume requiring the use of a large absorber unit and substantially all of the olefinic feedstock.

Therefore, conventional absorber systems are acceptable for applications where substantially all of the olefinic feedstock is fed through the absorber such that all of the available cobalt is returned to the oxo reactor together with the feedstock. However, instances where it is not desirable to pass all of the olefinic feedstock through the absorber section, conventional absorber systems have been found to be incapable of returning all of the available cobalt to the oxo reactor. This is because conventional absorbers operating under typical absorber conditions (i.e., 30° C. and 0.8 atm CO partial pressure) are only capable of absorbing approximately 0.3 weight % of cobalt (i.e., 3,000 ppm by weight of cobalt metal).

In some instances it is highly desirable to preheat a portion of the olefinic feedstock prior to its introduction into the oxo reactor. The preheated feedstock allows the hydroformylation reaction to proceed immediately without the necessary heat-up period. This can substantially decrease the overall time that it takes for the oxo reaction to proceed. However, if the cobalt-containing olefinic feedstock from the absorber is preheated, then the volatile cobalt compound contained therein will tend to plate out as highly undesirable cobalt metal.

The present inventor has developed an absorber system that is capable of absorbing substantially more cobalt per unit volume of olefinic feedstock than conventional absorber systems, i.e., a cobalt concentration of up to approximately 3.5 weight %. This cobalt concentration level is unattainable via conventional absorber systems.

The present inventor has developed a novel method and system for substantially increasing the cobalt concentration per unit volume of olefinic feedstock. This is accomplished by recycling a portion of the discharged liquid phase back to the absorber via a liquid hold-up reactor under predetermined operating conditions such that the concentration of non-volatile cobalt compound species in the liquid phase is increased due to the decomposition of the volatile cobalt compound.

The present invention attains such cobalt concentration levels by the incorporation of a means for passing the liquid phase discharged from the absorber unit through a liquid hold-up reactor and either returning the cobalt enhanced solution to the absorber or sending it on to the oxo reactor. The volume, temperature and pressure of the liquid hold-up reactor are adjusted so as to increase the rate at which volatile $HCo(CO)_4$ decomposes to a non-volatile species such acylcobalt carbonyl and/or $Co_2(CO)_8$. The present inventor has also discovered that the use of linear olefins as the feedstock also substantially increases the rate at which volatile cobalt compounds decompose to non-volatile cobalt compound species.

The present invention also provides many additional advantages which shall become apparent as described below.

SUMMARY OF THE INVENTION

A method for absorbing cobalt within an olefinic feedstock which comprises the steps of: introducing a volatile cobalt compound into an absorber; introducing the olefinic feedstock into the absorber substantially simultaneous with the volatile cobalt compound to form a cobalt-containing olefin mixture, the cobalt-containing olefin mixture having both volatile and non-volatile cobalt compound species entrained therein; withdrawing the cobalt-containing olefin mixture from the absorber; introducing at least a portion of the cobalt-containing olefin mixture into a reactor, wherein a substantial portion of the volatile cobalt compound entrained within the cobalt-containing olefin mixture decomposes to its non-volatile cobalt compound species such that a cobalt-containing olefin solution is formed; withdrawing the cobalt-containing olefin solution from the reactor; and recycling at least a portion of the cobalt-containing olefin solution to the absorber; whereby the cobalt-containing olefin solution has a cobalt concentration of up to about 3.5 weight %.

The reactor preferably has a temperature within the range from about 20 to about 100° C., a carbon monoxide partial pressure in the range from about 0 to about 3 atm and a residence time from about 0 to about 3 hours.

The absorber system according to the present invention preferably comprises an absorber unit which comprises an absorber chamber, a means for introducing a volatile cobalt compound to the absorber chamber, and a means for introducing an olefinic feedstock to the absorber chamber, the absorber unit being capable of forming a cobalt-containing olefin mixture; a liquid hold-up reactor attached to the absorber unit which is capable of decomposing volatile cobalt compounds contained within the cobalt-containing olefin mixture to their non-volatile species, whereby a cobalt-containing olefin solution is formed; and a recycle means disposed between the reactor and the absorber chamber, whereby a cobalt-containing olefin solution is formed.

The present invention is particularly useful for producing higher aldehydes and higher alcohols by hydroformylating an olefinic feedstock with synthesis gas in the presence of a cobalt-containing catalyst to form a crude product containing higher aldehyde, higher alcohol, secondary products and dissolved cobalt catalysts, and recycling the cobalt catalyst for continuous use in the hydroformylation process.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1:
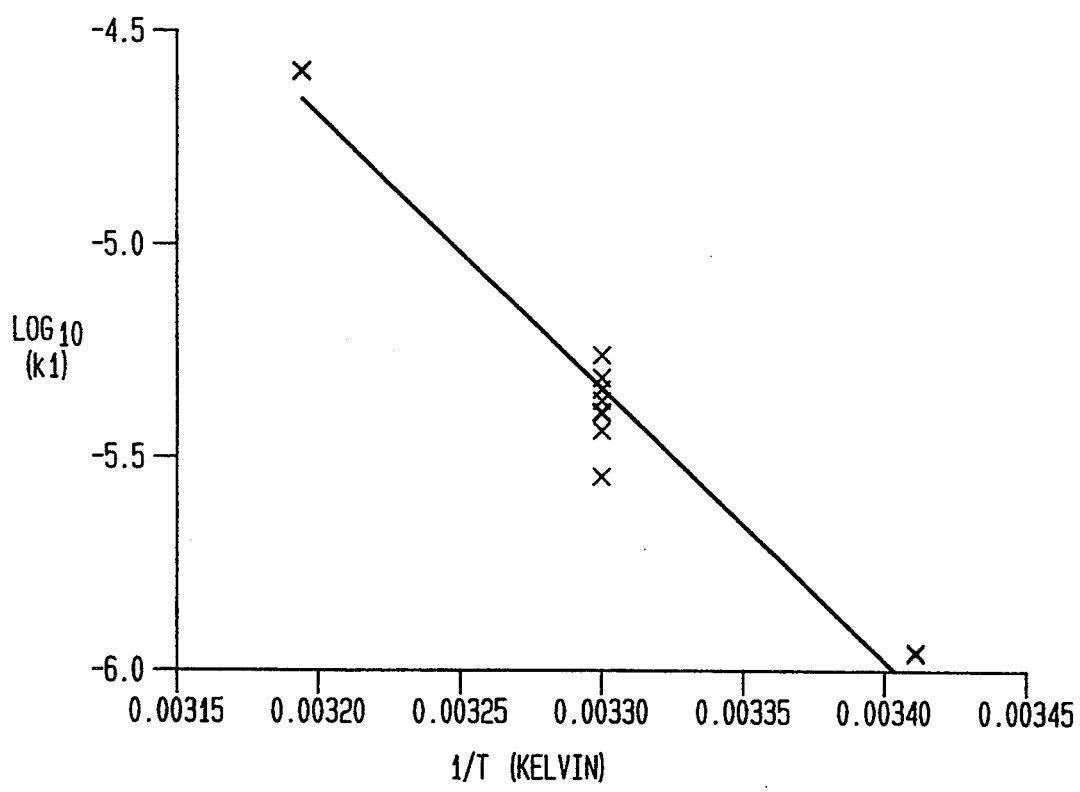
FIG. 1 is a graph plotting $\log_{10}(k1)$ versus the reciprocal temperature to determine k1, i.e., the rate constant for $HCo(CO)_4$ decomposition in non-reactive solvents such as paraffins.

In the process according to the present invention, cobalt is absorbed into an olefin feedstream from a gas stream of volatile $HCo(CO)_4$. The $HCo(CO)_4$ then reacts with the olefin to form non-volatile species. The volume, temperature, and pressure of the liquid hold-up reactor or tank are adjusted so that the $HCo(CO)_4$ is almost completely decomposed in the reactor. The solution discharged from the reactor contains little or no volatile cobalt compounds and it can be recycled back to the absorber for the purpose of absorbing additional cobalt and/or fed directly to the oxo reactor as the primary source of the cobalt catalyst used in the hydroformylation reaction. The recycle to feed ratio is adjusted to give the desired cobalt concentration in the feed to oxo ratio.

Moreover, this process allows the olefinic feedstock to be split into two parts with one part passing through the absorber section and the other part going directly to the oxo reactor. This has the advantage of allowing the operator to control the overall cobalt concentration of the oxo reactor by simply adjusting the amount of non-cobalt containing olefinic feedstock added thereto. Also the non-cobalt containing olefinic feedstock can be preheated at low pressure without causing cobalt plating in the preheater.

The present invention is particularly useful in producing higher aldehydes and higher alcohols by means of hydroformylating an olefinic feedstock with synthesis gas in the presence of a cobalt-containing catalyst to form a crude product containing higher aldehyde, higher alcohol, secondary products and dissolved cobalt catalysts; removing the cobalt catalysts from the crude product by the steps of: (a) contacting the crude product in a stripper-reactor with a stream of stripping gas in the presence of water and organic acid to entrain volatile cobalt compounds in the stripping gas, whereby the entrained volatile cobalt compounds are taken out overhead and organic hydroformylation reaction products and water containing water soluble cobaltous salts are taken out as bottoms; (b) withdrawing the organic hydroformylation reaction products and the water containing water soluble cobaltous salts from the stripper-reactor; and (c) withdrawing the stripping gas with the entrained volatile cobalt compounds from the stripper-reactor; withdrawing the bottoms of the stripper-reactor and separating the organic hydroformylation reaction products from the water containing water soluble cobaltous salts, whereby the organic hydroformylation reaction products are recovered and sent for further downstream treatment such as distillation or hydrogenation; introducing the stripping gas with entrained volatile cobalt compounds into an absorber; introducing the olefinic feedstock into the absorber together with the volatile cobalt compounds to form a cobalt-containing olefin mixture, the cobalt-containing olefin mixture having both volatile and non-volatile cobalt compound species entrained therein; withdrawing the cobalt-containing olefin mixture from the absorber; introducing at least a portion of the cobalt-containing olefin mixture into a liquid hold-up reactor, wherein a substantial portion of the volatile cobalt compounds entrained within the cobalt-containing olefin mixture decompose to non-volatile cobalt compound species such that a cobalt-containing olefin solution is formed; and withdrawing the cobalt-containing olefin solution from the reactor; whereby the cobalt-containing olefin solution has a cobalt concentration of up to about 3.5 weight %.

The present invention may also be used wherein volatile cobalt compounds are generated by the reaction of a cobalt carbonylate salt such as $NaCo(CO)_4$ (i.e., the salt is formed from the reaction product of $HCo(CO)_4$ and NaOH in a separator which is disposed upstream of the volatilization tower) with a strong acid (e.g., $H_2SO_4$) to produce $HCo(CO)_4$ in a volatilization tower. These volatile cobalt compounds can be entrained in a carrier gas stream, which transports them to the absorber.

It is preferable that the optional step of recycling at least a portion of the cobalt-containing olefin solution to the absorber be added such that the concentration of cobalt within the cobalt-containing olefin solution can be increased to such a level that all of the cobalt can be recycled to the oxo reactor.

The rate of decomposition of $HCo(CO)_4$ to $Co_2(CO)_8$ is substantially increased by controlling the operating conditions of the liquid hold-up reactor such that the temperature is maintained within the range from about 20 to about 100° C., the carbon monoxide partial pressure is maintained in the range from about 0 to about 3 atm and wherein the cobalt-containing olefin mixture is retained within the reactor for a period from about 0 to about 3 hours.

Figure 3:
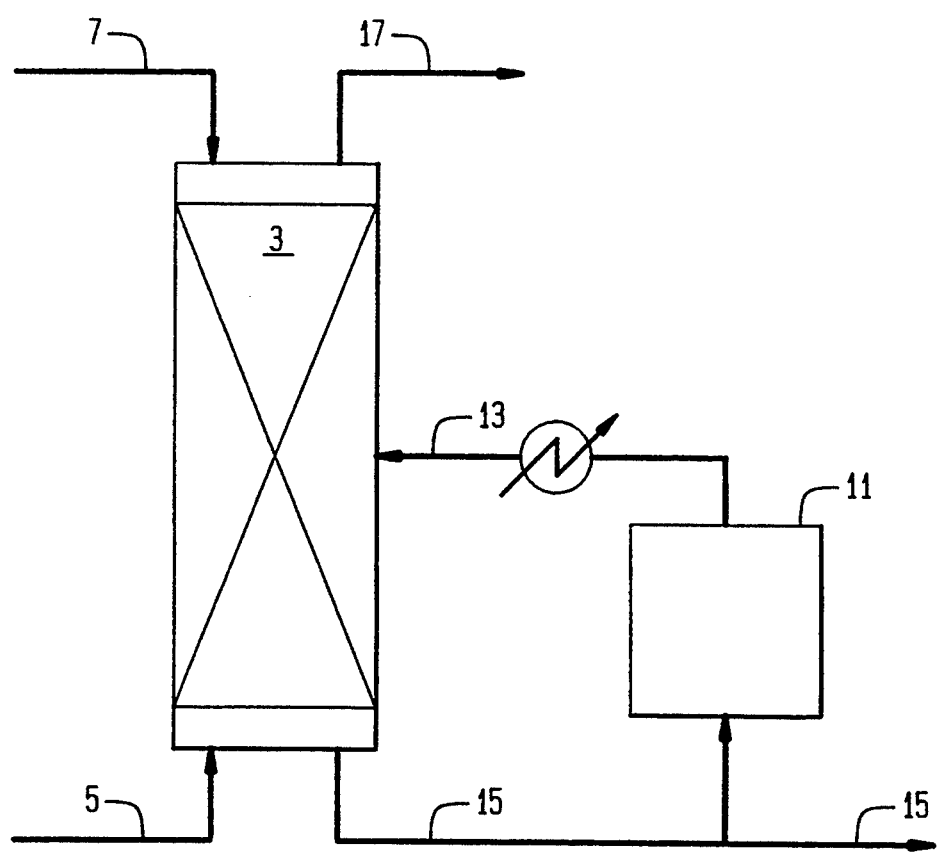
FIG. 3 is a schematic representation of an absorber with recycle and liquid hold-up reactor according to the present invention.

The present invention can best be understood by reference to FIG. 3 which schematically depicts the absorber system of the present invention which comprises: an absorber unit 1 which comprises an absorber chamber 3, a conduit means 5 for introducing a volatile cobalt compound to absorber chamber 3, and a conduit means 7 for introducing an olefinic feedstock to absorber chamber 3. Conduit means 5 is typically connected to a stripper reactor (not shown). Cobalt-containing olefin leaves the absorber via conduit 15 and is sent to the hydroformylation reaction. A portion of the olefin from conduit 15 may be removed via conduit 9 and is sent to the reactor vessel 11. The effluent from reactor 11 is recycled back to the absorber. Syn gas is taken out of absorber chamber 3 via conduit 17.

EXAMPLE 1

Figure 5:
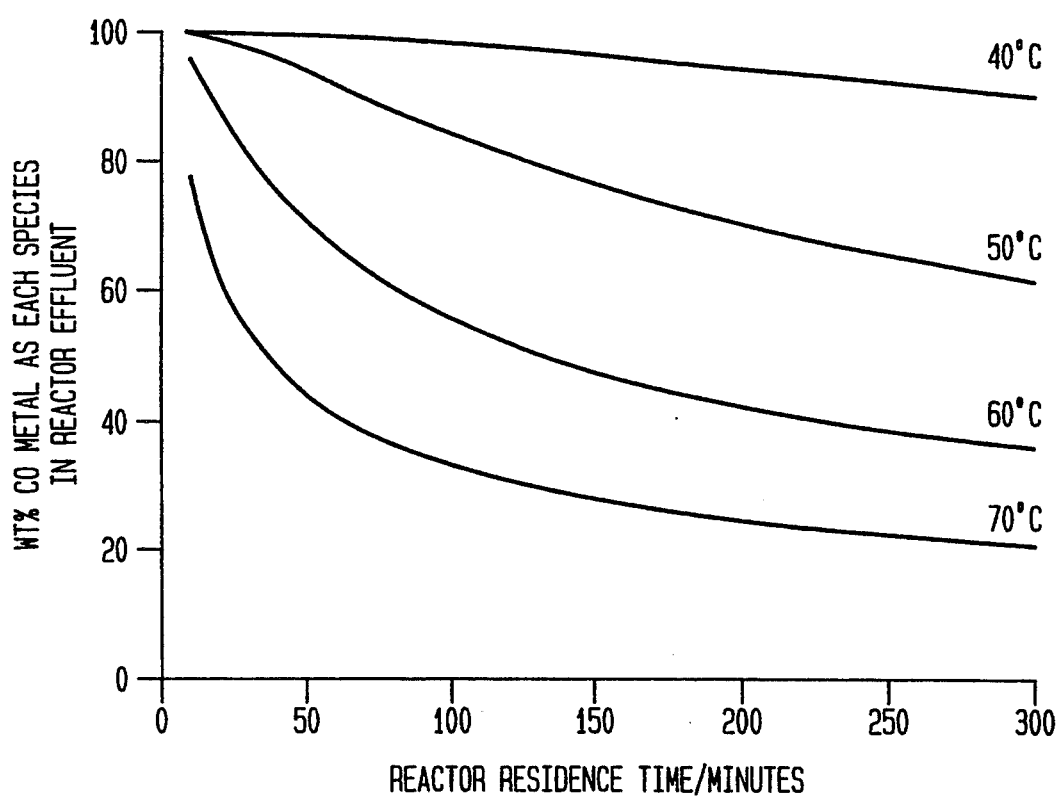
FIG. 5 illustrates the effect of temperature on $HCo(CO)_4$ conversion.
Figure 6:
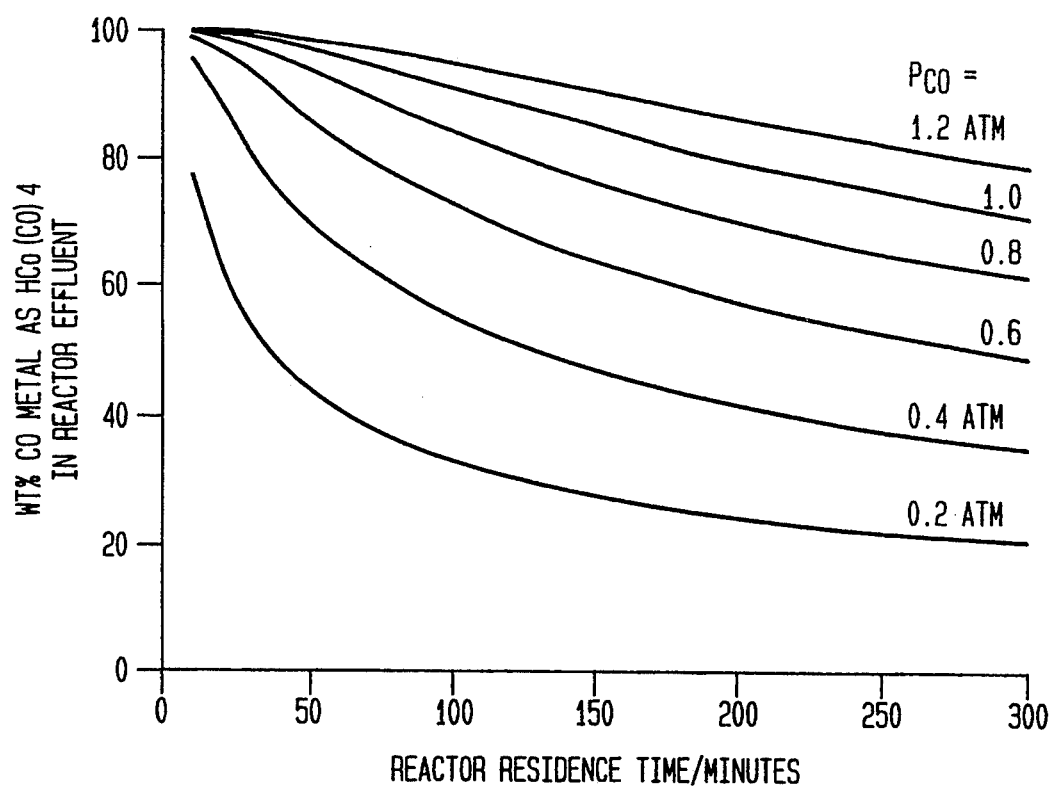
FIG. 6 illustrates the effect of carbon monoxide partial pressure on $HCo(CO)_4$ conversion.
Figure 7:
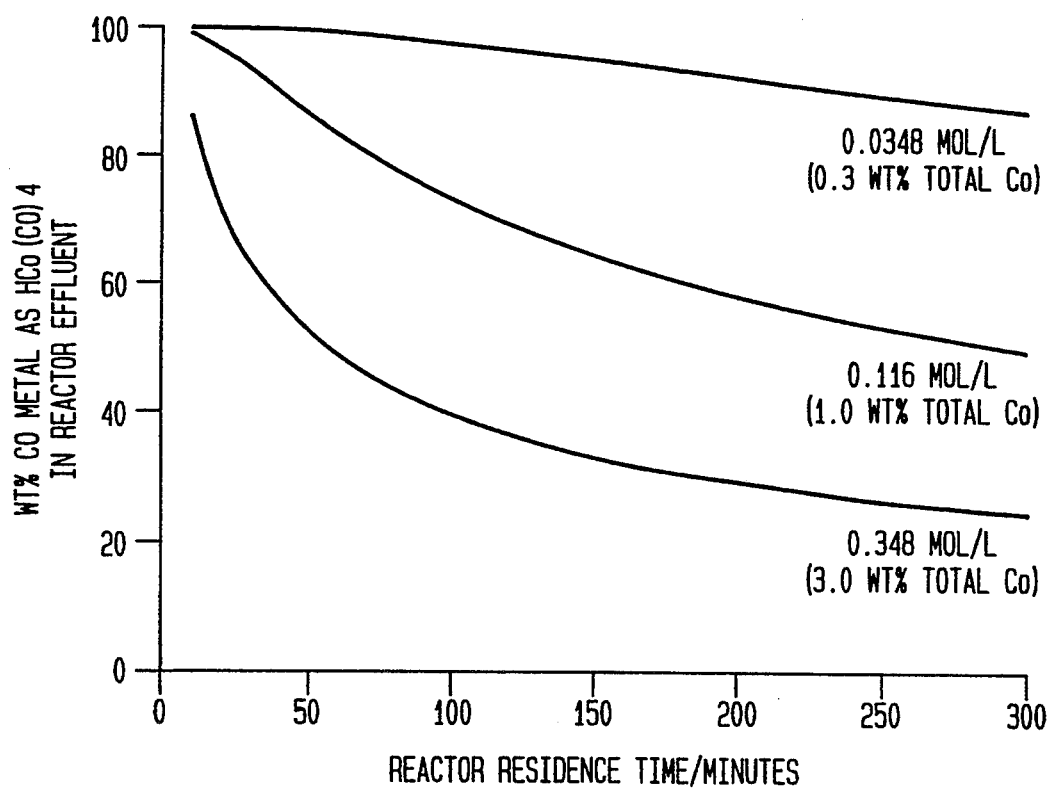
FIG. 7 illustrates the effect of total cobalt concentration on $HCo(CO)_4$ conversion.

The rates of decomposition of $HCo(CO)_4$ and $Co_2(CO)_8$, as depicted in FIGS. 5–7, were calculated using data from kinetic measurements reported in the available literature. The calculations show that at typical absorber conditions (i.e., 35° C., 0.8 atm CO partial pressure, 0.3% weight % total cobalt) the decomposition rate of $HCo(CO)_4$ is quite slow.

Generally, cobalt carbonyls decompose according to the following reactions:

$$2HCo(CO)_4 \rightarrow Co_2(CO)_8 + H_2 \quad (1)$$

$$2Co_2(CO)_8 \rightarrow Co_4(CO)_{12} + 4\,CO \quad (2)$$

$$3Co_2(CO)_8 + 12H_2O \rightarrow 2[Co(H_2O_6)]^{2+} + [Co(CO)_4]^-{}_2 + 8CO \quad (3)$$

The first and second reactions are well known and quite typical in the decomposition of cobalt carbonyls. The third reaction, disproportionation of $Co_2(CO)_8$, takes place in the presence of free or dissolved water. Moreover, in dry organics (e.g., olefins, paraffins, aldehydes, alcohols with three or more carbons) reaction (3) does not proceed.

In the mathematical models set forth below, it is assumed that the rate of reaction (3) is negligible compared with the rates of the other reactions because there is little water present.

KINETIC DATA

The rate expressions for reactions (1) and (2) are:

$$r1 = \frac{-d[HCo(CO)_4]}{dt} = \frac{k1[[HCo(CO)_4]^2[Co_2(CO)_8]]^{\frac{1}{2}}}{[CO]^2}$$

$$r2 = \frac{d[Co_4(CO)_{12}]}{dt} = \frac{k2\,[Co_2(CO)_8]^2}{[CO]^2}$$

where all concentrations are moles/liter in the liquid phase. The rate constant k1 is calculated from the rate data of Ungvary and Marko, J. Organomet. Chem., 193, 383–387, (1980), by plotting $\log_{10}(k1)$ versus the reciprocal temperature, as shown in FIG. 1. The rate constant k2 is given explicitly by Ungvary and Marko, J. Organomet. Chem., 71, 283–286, (1974). The rate constant expressions are:

$$\log_{10}(k1) = 15.722 - 6385.2/T$$

$$\log_{10}(k2) = 1.35 - 7100/T$$

where T is in Kelvins, k1 is in $(mol^{\frac{1}{2}} liter^{\frac{1}{2}} min^{-1})$, and k2 is in $(mol\,liter^{-1}\,sec^{-1})$.

CARBON MONOXIDE SOLUBILITY

Figure 2:
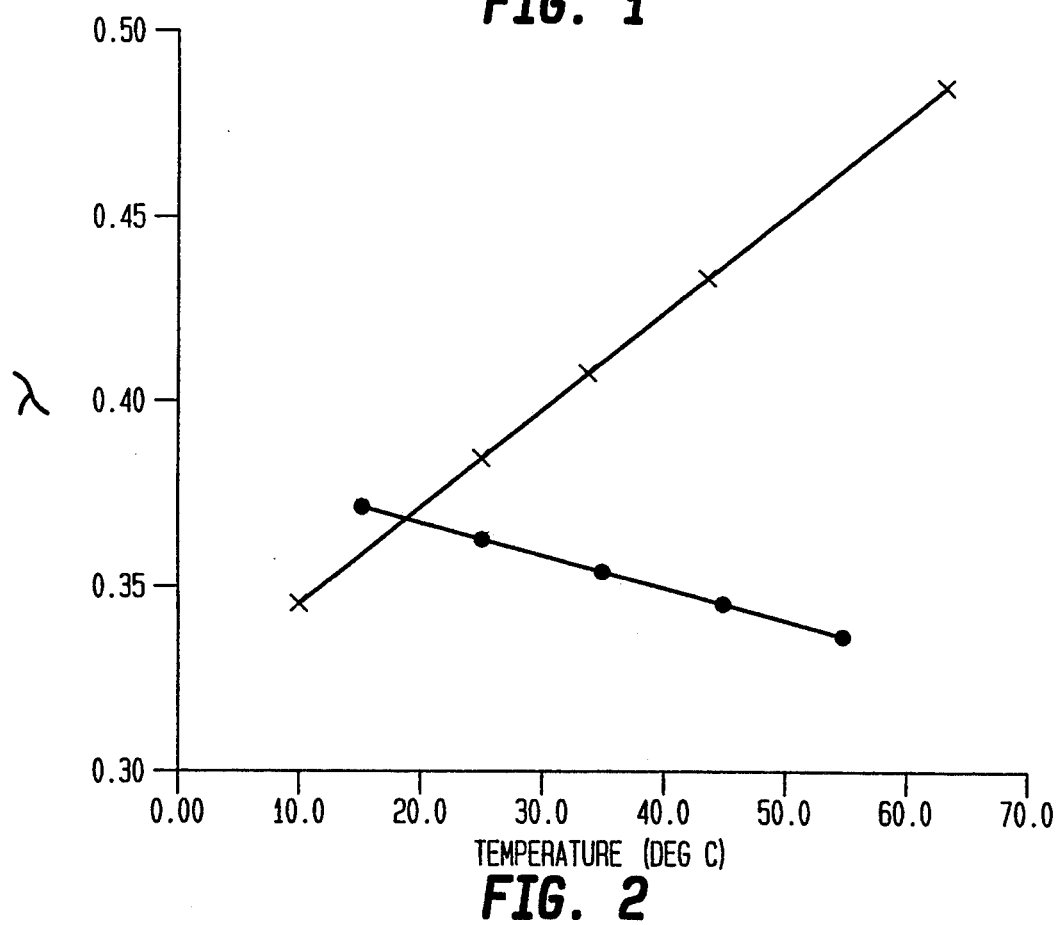
FIG. 2 is a graph plotting Oswald's coefficient ($\lambda$) versus temperature to demonstrate carbon monoxide solubility.

Ungvary gives solubility data for CO in 1-heptene (see Ungvary, Acta Chimica Acad. Sci. Hung., 111, 117–130, (1982)) and n-heptane (see Ungvary, J. Organomet. Chem., 36, 363 (1972)). The data are in the form of Oswald's coefficient ($\lambda$) versus temperature and are shown in FIG. 2. One unusual feature of the data is that the slope of CO solubility with temperature is positive for n-heptane and negative for 1-heptene. A constant value of $\lambda = 0.36$ was choose by the present inventor to represent an average for various olefin solvents.

TOTAL COBALT CONCENTRATION

The following conversion factor from weight percent total cobalt to moles per liter was used:

0.3 wt % total cobalt = 0.0348 mol $HCo(CO)_4$/liter.

STEADY-STATE MODEL

An absorber pump-around/olefin storage system in accordance with the present invention is shown in FIG. 3. The following assumptions where made: (1) $HCo(CO)_4$ is the only cobalt carbonyl species fed to the system; (2) temperature and CO partial pressure are constant; (3) the dissolved CO in the liquid is in equilibrium with the CO in the gas; and (4) only reactions (1) and (2) can proceed. The equations describing the exit concentrations of the three cobalt species are:

$$[HCo(Co)_4] = [HCo(Co)_4]_0 - r1\tau$$

$$[Co_4(CO)_{12}] = r2\tau$$

$$[Co_2(Co)_8] = (\tfrac{1}{2}r1 - 2r2)\tau$$

where $[HCo(CO)_4]_0$ is the entrance concentration of $HCo(CO)_4$ and $\tau$ is the residence time of the system.

The equations predict an increase in the $HCo(CO)_4$ decomposition rate as temperature increases, as CO partial pressure decreases, and as total cobalt concentration increases. The autocatalytic effect of $Co_2(CO)_8$ is observed in the shape of the conversion versus residence time curves.

Figure 4:
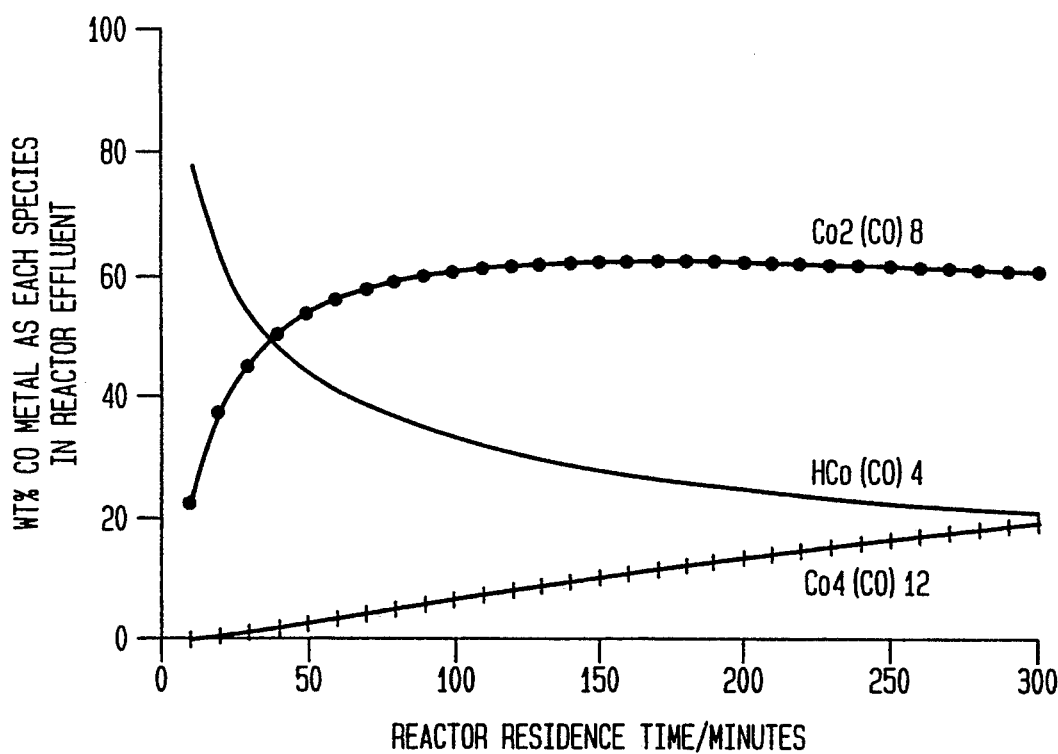
FIG. 4 shows the model solution for all three carbonyl species concentrations as a function of reactor residence time at 70° C. and 0.8 atm carbon monoxide partial pressure.

FIG. 4 shows the model solution for all three carbonyl species concentrations as a function of reactor residence time at 70° C. and 0.8 atm carbon monoxide (CO) partial pressure. $HCO(CO)_4$ decomposes to form $Co_2(CO)_8$ faster than $Co_2(CO)_8$ decomposes to form $Co_4(CO)_{12}$. Therefore, the $Co_2(CO)_8$ concentration can build up to a relatively high value before it declines. Also, the $Co_4(CO)_{12}$ is likely to react further to form heavier cobalt carbonyl complexes and eventually to form cobalt metal. Cobalt metal formation is not considered in this model, but at high temperature, low pressure, and sufficient residence time, cobalt metal will be the final product.

FIGS. 5–7 show the effect of various operating conditions on the $HCo(CO)_4$ concentration leaving the system. FIG. 5 studies the effect of temperature on $HCo(CO)_4$ conversion. At temperatures near those used in conventional absorbers (i.e., <40° C.), very little $HCo(CO)_4$ is converted over a period of six hours.

FIG. 6 studies the effect of CO partial pressure on $HCo(CO)_4$ conversion. CO partial pressure appears to the $-2$ power in the rate expression, thus the reaction rate is increased significantly by removing CO from the system.

FIG. 7 studies the effect of total cobalt concentration on the $HCo(CO)_4$ conversion. This calculation is done at 35° C. and 0.5 atm CO partial pressure, which could represent an atmospheric storage tank (1 atm of 50:50 syn gas) or an olefin-filled cobalt absorber in an oxo reaction process plant. At high cobalt concentration, much of the $HCo(CO)_4$ has decomposed in several hours. This is due to the second order dependence of reaction rate on $HCo(CO)_4$ concentration.

At typical conditions, the decomposition rate of $HCo(CO)_4$ is small. Thus an absorber pump-around or recycle without a reactor present is only effective hydraulically, and it cannot be used to significantly reduce the concentration of $HCo(CO)_4$ in the liquid. However, when a liquid hold-up reactor is disposed within the recycle conduit of the absorber such that the residence time is increased, temperature is increased and/or the CO partial pressure is reduced, then a significant amount of the $HCo(CO)_4$ will decompose to non-volatile cobalt compound species.

EXAMPLE 2

The vapor-liquid equilibrium of $HCo(CO)_4$ between syn gas and different organic solvents has been analyzed at atmospheric pressure and different temperatures by means of single staged absorption tests.

One purpose of this experiment was to compare the behavior of $HCo(CO)_4$ in linear olefins, branched olefins and isoparafins. A second purpose was to confirm existing literature data on $HCo(CO)_4$ vapor pressure.

A carbonylate water containing 1.96% Co was pumped by means of a metering pump into a glass stripper filled with 30 grams of a 25% sulfuric acid solution. The liberated $HCo(CO)_4$ was stripped out by means of a syn gas stream. By feeding the stripper with a constant flow of sodium carbonylate and by using a constant gas flow, it was possible to assure a constant cobalt concentration in the stripping gas.

The cobalt rich gas was sent through a glass absorber filled with 100 ml of an organic absorption medium. The absorption device had a sintered distribution plate allowing very fine dispersion of the gas through the liquid.

The absorber was put in a thermo-static bath, allowing it to operate at different temperatures. All of the tests were carried out at atmospheric pressure.

The cobalt, breaking through the absorber, was trapped in two bubblers which were connected in series, each of which contained 300 grams of a 2% caustic solution. The gas flow was measured with a wet gas-meter at the outlet of the second caustic bubbler.

At regular time intervals, samples were taken from the absorber and first caustic trap for cobalt analyses, while the total gas flow was recorded. At the end of the tests, the amount of cobalt trapped in the second bubbler was analyzed to close the cobalt material balance and to correct for the cobalt which slipped through the first bubbler.

All experimental data are grouped in Tables 1–6 below. These include tests at 20° C. and 40° C. for i-nonene, isopar E (i.e., a $C_9$ paraffin with less that 1 ppm of olefin) and n-decene-1.

i-Nonene and Isopar E at 20° C.

$HCo(CO)_4$ did not decompose to a non-volatile complex or to $Co_2(CO)_8$ in either i-nonene or isopar E at 20° C. This was demonstrated by the fact that in both cases 97% of the total cobalt content in the absorber (1.1 to 1.2 wt. % cobalt) remained stable and could be extracted as sodium carbonylate by treatment with a caustic solution after 30 minutes of testing. The distribution coefficients calculated as such reflected true vapor-liquid equilibrium (VLE) of the $HCo(CO)_4$. The $HCo(CO)_4$ vapor pressures derived from the distribution coefficients compare very well with those found in the literature. The measured vapor pressure ranged from between 197 mmHg to 220 mmHg, whereas the literature predicted 229 mmHg.

As such, an absorber running on branched olefins at low temperature (i.e., <20° C.) is characterized by physical distribution only. The results from this experiment are set forth below in Tables 1 and 2:

TABLE 1

| (Absorption Data for $HCo(CO)_4$ using i-Nonene) | | | | | | |
|---|---|---|---|---|---|---|
| Gas = | syn gas ($H_2$/CO = 1.2, 3% $CO_2$) | | | | | |
| Temperature = | 20° C. | | | | | |
| Pressure = | 1 ATMa | | | | | |
| Cobalt in Rich gas = | 0.7068 mol % | | | | | |
| Time (min.) | Liquid L | Total Gas | Gas/ Liquid Volume | (tot) Mol % | Y Mol % | K (tot) |
| 0–3 | 0.0993 | 9 | 91 | 0.066 | 0.008 | 0.121 |
| 3–6 | 0.0978 | 16 | 164 | 0.277 | 0.082 | 0.295 |
| 6–9 | 0.0958 | 24 | 251 | 0.611 | 0.135 | 0.221 |
| 9–12 | 0.0940 | 32 | 340 | 0.933 | 0.308 | 0.330 |
| 12–18 | 0.0909 | 53 | 583 | 1.312 | 0.404 | 0.308 |
| 18–24 | 0.0882 | 71 | 805 | 1.798 | 0.504 | 0.281 |
| 24–30 | 0.0864 | 89 | 1030 | 2.177 | 0.616 | 0.283 |

TABLE 2

| (Absorption Data for $HCo(CO)_4$ using Isopar E) | | | | | | |
|---|---|---|---|---|---|---|
| Gas = | syn gas ($H_2$/CO = 1.2, 3% $CO_2$) | | | | | |
| Temperature = | 20° C. | | | | | |
| Pressure = | 1 ATMa | | | | | |
| Cobalt in Rich gas = | 0.712 mol % | | | | | |
| Time (min.) | Liquid L | Total Gas | Gas/ Liquid Volume | (tot) Mol % | Y Mol % | K (tot) |
| 0–3 | 0.0981 | 10 | 102 | 0.0902 | 0.0016 | 0.0181 |
| 3–6 | 0.0952 | 17 | 179 | 0.3099 | 0.0579 | 0.1868 |
| 6–9 | 0.0924 | 26 | 261 | 0.5823 | 0.1270 | 0.2181 |
| 9–12 | 0.0905 | 34 | 376 | 0.8786 | 0.1811 | 0.2061 |
| 12–18 | 0.0863 | 63 | 614 | 1.3710 | 0.3446 | 0.2613 |
| 18–24 | 0.0822 | 52 | 876 | 2.0180 | 0.5411 | 0.2681 |

TABLE 2-continued

| (Absorption Data for HCo(CO)₄ using Isopar E) | | | | | |
|---|---|---|---|---|---|
| 24–30 | 0.0782 | 91 | 1164 | 2.5300 | 0.6181 | 0.2443 | i-Nonene and Isopar E at 40° C.

At higher temperatures $HCo(CO)_4$ showed more decomposition in i-nonene than in isopar E. In isopar E, after 30 minutes, 86% of the total cobalt content in the absorber (0.64 wt. % cobalt) was still stable, while for i-nonene this was only 52% of the total cobalt content (0.62 wt. % cobalt).

For both tests, the distribution coefficient between the free $HCo(CO)_4$ in the organic and the gas was calculated. As mentioned before, the fraction of free $HCo(CO)_4$ in the liquid was estimated by admitting, throughout the entire test, the same volatile/non-volatile ratio in the organic phase that was measured at the end of the experiment. The latter had quite a negative influence on the accuracy of the results in the case of i-nonene, due to the much higher decomposition rate observed in this experiment. A vapor pressure of 690 mmHg with i-nonene and of 590 mmHg with isopar E was found, whereas literature predicted 557 mmHg. It is clear that an absorber, using i-nonene at 40° C., will start to show some $HCo(CO)_4$ decomposition and thus no longer be characterized by physical distribution alone.

The results of this experiment are set forth below in Tables 3 and 4:

TABLE 3

| (Absorption Data for HCo(CO)₄ using i-Nonene) | | | | | | | |
|---|---|---|---|---|---|---|---|
| Gas = | | | syn gas (H₂/CO = 1.2, 3% CO₂) | | | | |
| Temperature = | | | 40° C. | | | | |
| Pressure = | | | 1 ATMa | | | | |
| Cobalt in Rich gas = | | | 0.6561 mol % | | | | |
| Time (min) | Liquid L | Total Gas | Gas/Liquid Volume | X (tot) Mol % | (HyCo) Mol % | Y Mol % | K (tot) | K (HyCo) |
| 0–3 | 0.1170 | 11 | 94 | 0.0647 | 0.0336 | 0.0065 | 0.1011 | 0.1946 |
| 3–6 | 0.1140 | 18 | 158 | 0.2152 | 0.1119 | 0.1367 | 0.6352 | 1.2216 |
| 6–9 | 0.1120 | 26 | 232 | 0.3816 | 0.1984 | 0.2147 | 0.5626 | 1.0822 |
| 9–12 | 0.1090 | 35 | 321 | 0.5281 | 0.2746 | 0.2912 | 0.5514 | 1.0605 |
| 12–18 | 0.1040 | 53 | 510 | 0.7112 | 0.3698 | 0.4119 | 0.5792 | 1.1138 |
| 18–24 | 0.0986 | 73 | 740 | 0.9990 | 0.5195 | 0.4517 | 0.4522 | 0.8695 |
| 24–30 | 0.0934 | 82 | 878 | 1.2590 | 0.6547 | 0.5940 | 0.4718 | 0.9073 |

TABLE 4

| (Absorption Data for HCo(CO)₄ using Isopar E) | | | | | | | |
|---|---|---|---|---|---|---|---|
| Gas = | | | syn gas (H₂/CO = 1.2, 3% CO₂) | | | | |
| Temperature = | | | 40° C. | | | | |
| Pressure = | | | 1 ATMa | | | | |
| Cobalt in Rich gas = | | | 0.7306 mol % | | | | |
| Time (min) | Liquid L | Total Gas | Gas/Liquid Volume | X (tot) Mol % | (HyCo) Mol % | Y Mol % | K (tot) | K (HyCo) |
| 0–3 | 0.0974 | 9 | 92 | 0.1203 | 0.1035 | 0.0809 | 0.6725 | 0.7816 |
| 3–6 | 0.0928 | 17 | 183 | 0.3518 | 0.3026 | 0.1881 | 0.5347 | 0.6216 |
| 6–9 | 0.0888 | 25 | 282 | 0.5610 | 0.4825 | 0.3787 | 0.6750 | 0.7849 |
| 9–13 | 0.0835 | 37 | 443 | 0.8217 | 0.7067 | 0.4726 | 0.5751 | 0.6687 |
| 13–16 | 0.0808 | 46 | 569 | 1.0163 | 0.8740 | 0.6530 | 0.6425 | 0.7471 |
| 16–19 | 0.0773 | 55 | 712 | 1.1167 | 0.9304 | 0.7690 | 0.6886 | 0.8265 |
| 19–25 | 0.0703 | 72 | 1024 | 1.2590 | 1.1396 | 0.7950 | 0.6315 | 0.6976 |
| 25–31 | 0.0636 | 87 | 1368 | 1.4170 | 1.2166 | 0.9910 | 0.6994 | 0.8146 |

N-Decene-1 at 20° C. and 40° C.

When n-decene-1 was used for absorption, the breakthrough from the absorber in both experiments was less than 1% of the total cobalt fed to it. At the end of the tests, 99.6% of all $HCo(CO)_4$ (i.e., 1.6 wt. % total cobalt in the olefin) had transformed into non-volatile species. At 40° C. very low distribution factors were measured, i.e., an average value of 0.0017 mol % Co in gas/mol % total Co in liquid. At 20° C. the distribution factor calculated instantaneously after each sampling period initially showed values comparable to those found for i-nonene or isopar E (i.e., between 0.21 to 0.31 mol % in gas/mol % in liquid), but as the total cobalt concentration in the liquid began to increase, the distribution coefficient rapidly dropped to very low levels (see Table 5 below).

The decomposition of $HCo(CO)_4$ to non-volatile species occurs so fast in a linear olefin that it can be concluded that for these grades the absorber will act as a reactor rather than being characterized by physical distribution.

The results of this experiment are set forth below in Tables 5 and 6:

TABLE 5

| (Absorption Data for HCo(CO)₄ using N-Decene-1) | | | | | | |
|---|---|---|---|---|---|---|
| Gas = | | | syn gas (H₂/CO = 1.2, 3% CO₂) | | | |
| Temperature = | | | 20° C. | | | |
| Pressure = | | | 1 ATMa | | | |
| Cobalt in Rich gas = | | | 0.6005 mol % | | | |
| Time (min.) | Liquid L | Total Gas | Gas/Liquid Volume | (tot) Mol % | Y Mol % | K (tot) |
| 0–3 | 0.1000 | 10 | 100 | 0.0892 | 0.0196 | 0.2197 |
| 3–6 | 0.0972 | 19 | 195 | 0.3009 | 0.0929 | 0.3087 |
| 6–9 | 0.0966 | 27 | 280 | 0.5297 | 0.1390 | 0.2624 |
| 9–12 | 0.0961 | 36 | 375 | 0.8096 | 0.0910 | 0.1124 |
| 12–18 | 0.0955 | 55 | 576 | 1.3980 | 0.0220 | 0.0157 |
| 18–24 | 0.0948 | 66 | 696 | 2.3020 | 0.0370 | 0.0161 |

TABLE 5-continued

| (Absorption Data for HCo(CO)$_4$ using N-Decene-1) | | | | | |
|---|---|---|---|---|---|
| 24–30 | 0.0942 | 84 | 892 | 3.2370 | 0.0089 | 0.0027 |

TABLE 6

(Absorption Data for HCo(CO)$_4$ using N-Decene-1)

| Gas = | syn gas (H$_2$/CO = 1.2, 3% CO$_2$) |
|---|---|
| Temperature = | 40° C. |
| Pressure = | 1 ATMa |
| Cobalt in Rich gas = | 0.6551 mol % |

| Time (min.) | Liquid L | Total Gas | Gas/Liquid Volume | (tot) Mol % | Y Mol % | K (tot) |
|---|---|---|---|---|---|---|
| 0–3 | 0.1007 | 7 | 70 | 0.039 | 0.0000 | 0.0000 |
| 3–6 | 0.0964 | 12 | 124 | 0.2451 | 0.0000 | 0.0000 |
| 6–9 | 0.0919 | 19 | 207 | 0.5420 | 0.0000 | 0.0000 |
| 9–12 | 0.0907 | 28 | 309 | 0.9014 | 0.0024 | 0.0026 |
| 12–15 | 0.0896 | 36 | 402 | 1.2956 | 0.0036 | 0.0049 |
| 15–18 | 0.0888 | 45 | 507 | 2.0279 | 0.0069 | 0.0034 |
| 18–24 | 0.0878 | 65 | 740 | 2.7973 | 0.0050 | 0.0018 |
| 24–30 | 0.0870 | 84 | 966 | 3.3265 | 0.0027 | 0.0008 |

When linear decene-1 is used as the olefin, it appears that all HCo(CO)$_4$ instantaneously decomposes to non-volatile species. The latter reaction is so rapid that even a single absorption step, with very short contact time between gas and liquid, is able to retain over 99% of all cobalt from the inlet gas stream at both 20° C. and 40° C.

An absorber operating on linear decene will therefore fully work as a reactor. That is, the very low distribution factors calculated for n-decene indicated the enhanced efficiency of the absorber due to the rapid HCo(CO)$_4$ decomposition in linear olefins.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A method for absorbing cobalt within an olefinic feedstock which comprises:
   introducing a volatile cobalt compound into an absorber, said volatile cobalt compound comprising HCo(CO)$_4$;
   introducing said olefinic feedstock into said absorber together with said volatile cobalt compound to form a cobalt-containing olefin mixture, said cobalt-containing olefin mixture having both volatile and non-volatile cobalt compound species entrained therein, said non-volatile cobalt compound species are selected from the group consisting of: Co$_2$(CO)$_8$, Co$_4$(CO)$_{12}$ and mixtures thereof;
   withdrawing said cobalt-containing olefin mixture from said absorber;
   introducing at least a portion of cobalt-containing olefin mixture into a reactor having a temperature within the range between about 20 to about 100° C. and a carbon monoxide partial pressure in the range between about 0 to about 3 atm, wherein a substantial portion of said volatile cobalt compound entrained within said cobalt-containing olefin mixture decomposes to its non-volatile cobalt compound species such that a cobalt-containing olefin solution is formed; and
   withdrawing said cobalt-containing olefin solution from said reactor; whereby said cobalt-containing olefin solution has a cobalt concentration of up to about 3.5 weight %.

2. The method according to claim 1 further comprising the step of recycling at least a portion of said cobalt-containing olefin solution to said absorber.

3. The method according to claim 1 wherein said cobalt-containing olefin mixture is retained within said reactor for a period between about 0–3 hours.

4. The method according to claim 1 wherein said olefinic feedstock is either branched or linear C$_6$ to C$_{12}$ olefins.

5. An absorber system which comprises:
   an absorber unit which comprises an absorber chamber, a means for introducing a volatile cobalt compound to said absorber chamber, said volatile cobalt compound comprising HCo(CO)$_4$, and a means for introducing an olefinic feedstock to said absorber chamber, said absorber unit being capable of forming a cobalt-containing olefin mixture; and
   a reactor having a temperature within the range between about 20° to about 100° C. and a carbon monoxide partial pressure in the range between about 0 to about 3 atm is attached to said absorber unit which is capable of decomposing volatile cobalt compounds contained within said cobalt-containing olefin mixture to its non-volatile species selected from the group consisting of: Co$_2$(CO)$_8$, Co$_4$(CO)$_{12}$ and mixtures thereof, whereby a cobalt-containing olefin solution is formed.

6. The absorber system according to claim 5 further comprising a recycle means capable of recycling at least a portion of said cobalt-containing olefin solution to said absorber chamber.

7. The absorber system according to claim 5 wherein said reactor comprises a means for providing a residence time for said cobalt-containing olefin mixture in the range between about 0 to about 3 hours.

8. A method for producing aldehydes and alcohols which comprises:
   hydroformylating an olefinic feedstock with synthesis gas in the presence of a cobalt carbonyl catalyst to form a crude product containing aldehydes, alcohols, secondary products and dissolved cobalt carbonyl catalysts;
   removing said cobalt carbonyl catalysts from said crude product by the steps of: (a) contacting said crude product in a stripper-reactor with a stream of stripping gas in the presence of water and organic acid to entrain volatile cobalt compounds comprising HCo(CO)$_4$ in said stripping gas, whereby the entrained volatile cobalt compounds are taken out overhead and organic hydroformylation reaction products and water containing water soluble cobaltous salts are taken out as bottoms; (b) withdrawing said organic hydroformylation reaction products and said water containing water soluble cobaltous salts from said stripper-reactor; and (c) withdrawing the stripping gas with said entrained volatile cobalt compounds from said stripper-reactor;
   withdrawing said bottoms of said stripper-reactor and separating said organic hydroformylation reaction products from said water containing water soluble cobaltous salts, whereby said organic hydroformylation reaction products are recovered and sent for further downstream treatment such as distillation or hydrogenation;

introducing said stripping gas with entrained volatile cobalt compounds into an absorber;

introducing said olefinic feedstock into said absorber together with said volatile cobalt compounds to form a cobalt-containing olefin mixture, said cobalt-containing olefin mixture having both volatile and non-volatile cobalt compound species entrained therein, said non-volatile cobalt compound species are selected from the group consisting of: $Co_2(CO)_8$, $Co_4(CO)_{12}$ and mixtures thereof;

withdrawing said cobalt-containing olefin mixture from said absorber;

introducing cobalt-containing olefin mixture into a reactor having a temperature within the range between about 20° to about 100° C. and a carbon monoxide partial pressure in the range between about 0 to about 3 atm, wherein a substantial portion of said volatile cobalt compound entrained within said cobalt-containing olefin mixture decompose to its non-volatile cobalt compound species such that a cobalt-containing olefin solution is formed; and withdrawing at least a portion of said cobalt-containing olefin solution from said reactor; whereby said cobalt-containing olefin solution has a cobalt concentration of up to about 3.5 weight %.

9. The method according to claim 8 further comprising the step of recycling at least a portion of said cobalt-containing olefin solution to said absorber.

10. A method for producing aldehydes and alcohols which comprises:

hydroformylating an olefinic feedstock with synthesis gas in the presence of a cobalt carbonyl catalyst to form a crude product containing aldehydes, alcohols, secondary products and dissolved cobalt carbonyl catalysts;

removing said cobalt carbonyl catalysts from said crude product by the steps of: (a) mixing said crude product in a separator with a salt solution to form a cobalt carbonylate salt product as bottoms and wherein organic hydroformylation reaction products are taken overhead; (b) contacting said cobalt carbonylate salt product in a volatilization tower with a stream of carrier gas in the presence of water and an inorganic acid to form volatile cobalt compounds which are entrained in said carrier gas, whereby the entrained volatile cobalt compounds are taken out overhead; and (c) withdrawing the carrier gas with said entrained volatile cobalt compounds from said volatilization tower;

withdrawing said organic hydroformylation reaction products from said separator, whereby said organic hydroformylation reaction products are recovered and sent for further downstream treatment such as distillation or hydrogenation;

introducing said carrier gas with entrained volatile cobalt compounds into an absorber;

introducing said olefinic feedstock into said absorber together with said volatile cobalt compounds to form a cobalt-containing olefin mixture, said cobalt-containing olefin mixture having both volatile and non-volatile cobalt compound species entrained therein, said non-volatile cobalt compound species are selected from the group consisting of: $Co_2(CO)_8$, $Co_4(CO)_{12}$ and mixtures thereof;

withdrawing said cobalt-containing olefin mixture from said absorber;

introducing cobalt-containing olefin mixture into a reactor having a temperature within the range between about 20° to about 100° C. and a carbon monoxide partial pressure in the range between about 0 to about 3 atm, wherein a substantial portion of said volatile cobalt compound entrained within said cobalt-containing olefin mixture decomposes to its non-volatile cobalt compound species such that a cobalt-containing olefin solution is formed; and withdrawing at least a portion of said cobalt-containing olefin solution from said reactor; whereby said cobalt-containing olefin solution has a cobalt concentration of up to about 3.5 weight %.

11. The method according to claim 10 further comprising the step of recycling at least a portion of said cobalt-containing olefin solution to said absorber.

12. The method according to claim 8 wherein said olefinic feedstock is either branched or linear $C_6$ to $C_{12}$ olefins.

13. The method according to claim 8 wherein said aldehydes and alcohols are either branched or linear $C_7$ to $C_{13}$ aldehydes and alcohols.

14. The method according to claim 10 wherein said olefinic feedstock is either branched or linear $C_6$ to $C_{12}$ olefins.

15. The method according to claim 10 wherein said aldehydes and alcohols are either branched or linear $C_7$ to $C_{13}$ aldehydes and alcohols.

* * * * *